United States Patent [19]

Decker et al.

[11] Patent Number: 5,721,266

[45] Date of Patent: Feb. 24, 1998

[54] SUBSTITUTED IMIDAZOLINYL-IMIDAZOLINES AS ANTAGONISTS OF SH-2 BINDING AND THERAPEUTIC USES THEREOF

[75] Inventors: Stuart James Decker, Ann Arbor; David William Fry, Ypsilanti; James Marino Hamby; Alan Robert Saltiel, both of Ann Arbor, all of Mich.

[73] Assignee: Warner-Lambert Company, Morris Plains, N.J.

[21] Appl. No.: 312,253

[22] Filed: Sep. 26, 1994

Related U.S. Application Data

[63] Continuation-in-part of Ser. No. 68,863, May 28, 1993, abandoned.

[51] Int. Cl.[6] ............................. A01N 43/50
[52] U.S. Cl. ................. 514/398; 514/400; 514/401; 514/402
[58] Field of Search ............... 514/398, 400, 514/401, 402

[56] References Cited

U.S. PATENT DOCUMENTS 3,840,554 10/1974 Wittekind et al. ............... 260/309.6
3,905,992 9/1975 Wittekind et al. ............... 260/309.6

*Primary Examiner*—James J. Seidleck
*Assistant Examiner*—Michael A. Williamson
*Attorney, Agent, or Firm*—Francis J. Tinney

[57] ABSTRACT

Methods of treating proliferative diseases or viral, inflammatory, allergic and cardiovascular diseases, and restenosis are disclosed. The present invention demonstrates the use of N,N'-piperazinylbis-[2-amino-1-imidazolin-2-yl)-2-imidazolines], 2-amino-1-(2-imidazolin-2-yl)-2-imidazolines, and N,N'-alkylene-bis[2-amino-1-(2-imidazolin-2-yl)-2-imidazolines], their derivatives, and salts thereof, to antagonize the association of a protein tyrosine kinase with a substrate regulatory protein. The present invention also demonstrates the use of pharmaceutical compositions employing N,N'-piperazinylbis[2-amino-1-imidazolin-2-yl)-2-imidazolines], 2-amino-1-(2-imidazolin-2-yl)-2-imidazolines, and N,N'-alkylenebis-[2-amino-1-(2-imidazolin-2-yl)-2-imidazolines], their derivatives, and salts thereof, to antagonize the association of a protein tyrosine kinase with substrate regulatory protein. The present invention also relates to novel N,N'-piperazinylbis[2-amino-1-imidazolin-2-yl)-2-imidazolines].

11 Claims, 3 Drawing Sheets

SUBSTITUTED IMIDAZOLINYL-IMIDAZOLINES AS ANTAGONISTS OF SH-2 BINDING AND THERAPEUTIC USES THEREOF

CROSS-REFERENCE TO RELATED APPLICATIONS

This is a continuation-in-part application of U.S. patent application Ser. No. 08/068,863 filed May 28, 1993, now abandoned.

BACKGROUND OF THE INVENTION

1. Field of the Invention

The present invention relates to novel N,N'-piperazinylbis [2-amino-1-(2-imidazolin-2-yl)-2-imidazolines], and novel therapeutic uses of known compounds, 2-amino-1-(2-imidazolin-2-yl)-2-imidazolines and N,N'-alkylenebis[2-amino-1-(2-imidazolin-2-yl)-2-imidazolines], their derivatives, and pharmaceutically acceptable salts in the control of proliferative diseases such as cancer and psoriasis and in the treatment of viral, inflammatory, allergic and cardiovascular disease, and restenosis. This invention further relates to methods of treatment employing pharmaceutical compositions containing the compounds disclosed herein.

2. Background

Many of the signal transduction pathways that regulate a variety of cellular processes including the differentiation and proliferation of normal and malignant cells operate through growth factor receptors or proto-oncogene encoded growth factor receptors which possess intrinsic tyrosine kinase activity. This class of receptor includes, but is not limited to, the epidermal growth factor receptor (EGFR), fibroblast growth factor receptor (FGFR), macrophage colony stimulating factor receptor (CSF), and the platelet derived growth factor receptor (PDGFR). Growth factor binding to these receptors results in receptor autophosphorylation, activation of the receptor tyrosine kinase (RTK), and the phosphorylation of endogenous regulatory proteins participating in the signal transduction pathway. It is the phosphorylation of cellular proteins by these protein tyrosine kinases (PTKs) that, in turn, regulates the signaling pathways controlling many cellular activities, including mitogenesis, cell growth, and differentiation.

PDGFR activation and signal transduction play an important role in the proliferation and directed migration of vascular smooth muscle cells (VSMC). Abnormalities in the PDGFR signaling pathway have been implicated in such processes as vascular remodeling, restenosis, and atherosclerosis. Platelet-derived growth factor (PDGF) has been identified as one of the most potent endogenous VSMC mitogens and chemo-attractants. Elevated vascular mRNA expression of PDGF-A and -B chains and PDGF receptors has been observed in balloon-injured rat carotid arteries (*J. Cell. Biol.* 111:2149–2158 (1990)). In this injury model, infusion of PDGF also greatly increases intimal thickening and migration of VSMC (*J. Clin. Invest.* 89:507–511 (1992)). Tyrphostin tyrosine kinase inhibitors which block the PDGF signal transduction pathway have been shown to inhibit neointimal formation in a rat model of restenosis (*Drug Development Research* 29:158–166 (1993)). Furthermore, PDGF-neutralizing antibodies significantly reduce intimal thickening following balloon injury (Science 253:1129–1132 (1991)).

Both acidic fibroblast growth factor (aFGF) and basic fibroblast growth factor (bFGF) have many biological activities, including the ability to promote cellular proliferation and differentiation. Direct evidence in support of FGF involvement in vascular smooth muscle proliferation (VSMC) has been reported by Lindner and Reidy (*Proc. Natl. Acad. Sci. USA* 88:3739–3743 (1991)) who demonstrate that the systemic injection of a neutralizing antibody against bFGF prior to balloon angioplasty of rat carotid arteries inhibited injury-induced medial SMC proliferation by greater than 80% when measured 2 days after injury. It is likely that bFGF released from damaged cells is acting in a paracrine manner to induce VSMC growth. Recently, Lindner and Reidy (*Cir. Res.* 73:589–595 (1993)) demonstrated an increased expression of both mRNA and bFGF and FGFR-1 in replicating VSMCs and endothelium in en face preparations of balloon-injured rat carotid arteries. The data provides evidence that in injured arteries the ligand/receptor system of bFGF and FGFR-1 may be involved in the continued proliferative response of VSMCs leading to neointimal formation.

The receptor autophosphorylation sites serve as high-affinity binding sites for substrate proteins containing a specific amino acid sequence called a Src-homology 2 (SH-2) domain (*Science* 252:668 (1991)). SH-2 domains are sequences of about 100 amino acids found in the noncatalytic region of the src family of cytoplasmic (nonreceptor) protein tyrosine kinases (TKs). SH-2 domains have also been identified in a functionally diverse group of cytoplasmic proteins some of which are substrates for the growth factor receptor TKs. These proteins are involved in cellular signaling and transformation and include, but are not limited to, the following: phospholipase C$\gamma$1 (PLC$\gamma$1), ras GTPase activator protein (GAP), and the p85 subunit of phosphatidylinositol 3-kinase (p85/PI-3K). The compounds included in this invention selectively inhibit the binding of SH-2-containing proteins to certain receptor or oncogenic TKs or their substrates. Inhibition of this binding can block important interactions between the receptor or oncogenic TKs and relevant effector proteins and thereby disrupt or alter cellular signal transduction pathways utilized in some malignant and other hyperproliferative diseases. In virtually all cases of chronic myelogenous leukemia, the transforming gene, bcr-abl, contains an SH-2 domain that is essential for transforming potential (*EMBO Journal* 8:449 (1989); *Molecular and Cellular Biology* 12:609 (1992)). It has also been previously demonstrated that uncoupling the PTK from the signal transduction pathway results therapeutically in antitumor activity. Antitumor activity for TK inhibitors has been demonstrated both in vitro and in vivo (*J. Antibiot.* 39:170 (1986); *Eur. J. Cancer* 26(6):722 (1990); *J. Med. Chem.* 32:2344 (1989); *J. Med. Chem.* 34:1896 (1991); *Cancer Res.* 51:4430 (1991); *J. Med. Chem.* 34:2328 (1991); *Helv. Chim. Acta.* 75:696 (1992); *Cancer Res.* 52:4492 (1992)).

It has been suggested that the SH-2 domain(s) in these substrate proteins or oncogenic tyrosine kinases themselves mediate their selective binding to activated (phosphorylated) proteins (see *EMBO Journal* 11:1365 (1992)). Specific SH-2 domains bind to certain protein amino acid sequence motifs at tyrosine phosphorylation sites. The precise phosphotyrosine binding site or sites on TK receptors or substrates for some SH-2 containing substrate proteins have been suggested. For example, the high-affinity binding between the EGFR and the SH-2 domains of PLC-$\gamma$ is likely to require phosphorylation of tyrosine (Y) 992 (*J. Biol. Chem.* 255:23634–23639 (1993), *EMBO Journal* 11(2):559 (1992)). For the FGF receptor (flg), Y766 may represent the PLC-SH-2 binding site (Mohammadi M, et al., *Molecular and Cellular Biology* 11(10):5068–5078 (1991)).

Specific binding sites for SH-2-containing signaling proteins created by receptor or substrate phosphorylation may prescribe specificity for substrate binding. Likewise, the relative affinity and specificity with which different substrates bind to the same receptor can be predicted by direct binding analyses using recombinant proteins (*Proc. Natl. Acad. Sci. USA* 89:9559 (1992)). It is these parameters that control the course and regulation of cellular signaling (*J. Biol. Chem.* 20:14138 (1992)). Therefore, it may be possible to use sequence motifs identified by site directed mutagenesis to predict which substrates are likely to bind to which receptors at which sites.

U.S. Pat. Nos. 3,666,767, 3,798,232, 3,835,142, 3,840,554, and 3,927,022 disclose the 2-amino-1-(2-imidazolin-2-yl)-2-imidazoline compounds of the instant invention, methods for preparing them, and their use as antiarrhythmic and antibacterial agents. These patents are hereby incorporated by reference.

U.S. Pat. No. 3,905,992 discloses the N,N'-alkylenebis[2-amino-1-(2-imidazolin-2-yl)-2-imidazoline compounds of the instant invention, methods for preparing them, and their use as hypotensive agents. This patent is also hereby incorporated by reference.

In addition, several articles have been published which discuss the binding of Src homology 2 domain to activated growth factor receptors. These articles discuss several principles and experimental procedures which indicate the background of the invention or illustrate the state of the art to the reader. These articles are hereby incorporated by reference.

Activation of Phosphatidylinositol-3-Kinase by Nerve Growth Factor Involves Indirect Coupling of the trk Proto-Oncogene With Src Homology 2 Domains (*Neuron* 9:769–777 (1991)); Nerve Growth Factor Stimulates the Tyrosine Phosphorylation of a 38-kDa Protein That Specifically Associates With the Src Homology Domain of Phospholipase C-λ1 (*Journal of Biologic Chemistry* 267(30):21601–21606 (1992)); Direct Analysis of the Binding of Src-Homology 2 Domains of Phospholipase C to the Activated Epidermal Growth Factor Receptor (*Proc. Natl. Acad. Sci. USA* 89:9559–9563 (1991)). Direct Analysis of the Binding of the abl Src Homology 2 Domain to the Activated Epidermal Growth Factor Receptor (*J. Biol. Chem.* 268:1775–1779 (1993)). Sequence specificity in the recognition of the epidermal growth factor receptor by the abl Src homology 2 domain (*Oncogene* 9:1379–1385 (1994)). Sequence specificity in recognition of the Epidermal Growth Factor Receptor by Protein Tyrosine Phosphatase IB (*J. Biol. Chem.* 268:23634–23639 (1993)).

There is no disclosure in the above references that teach or suggest the present invention's novel uses of compounds to treat proliferative diseases or viral, inflammatory, allergic and cardiovascular diseases, and restenosis.

SUMMARY OF THE INVENTION

It has been found that the compounds of the present invention, and their derivatives, have the ability to substantially inhibit the association of a tyrosine phosphorylated protein with SH-2 containing substrate proteins. In particular, this invention pertains to novel N,N'-piperazinylbis[2-amino-1-(2-imidazolin-2-yl-2-imidazolines] as well as the use of 2-amino-1-(2-imidazolin-2-yl)-2-imidazolines and N,N'-alkylenebis[2-amino-1-(2-imidazolin-2-yl)-2-imidazolines], their derivatives, and pharmaceutically acceptable salts to substantially inhibit the binding of the SH-2 domain of abl to the EGF receptor.

Without wishing to be bound by theory, it is believed that the compounds substantially inhibit the binding of the SH-2 domain of abl to the EGF receptor by competitive inhibition. In so doing, the compounds may interfere with or modulate the association of this oncogene protein with its authentic cellular effector(s) and effectively uncouple the oncogene from the signal transduction pathway. In tumor cells, this can lead to the restoration of the normal regulation of cell growth and differentiation. Thus, the compounds of the present invention are useful in controlling and treating tumors. For example, the compounds of the present invention are useful in controlling and treating tumors such as: human chronic myelogenous leukemia; human acute myelogenous leukemia; human acute lymphoblastic leukemia; human epidermoid carcinoma; human colon carcinoma; breast adenocarcinoma; and the like.

This invention also pertains to the use of pharmaceutical compositions containing the compounds disclosed herein to inhibit the binding of the SH-2 domain of abl to the EGF receptor or its relevant tyrosine phosphorylated binding protein. Moreover, these compounds can block other SH-2-tyrosine kinase interactions that may result in the proliferation of other cell types involved in inflammation, allergy, cardiovascular disease, and restenosis.

BRIEF DESCRIPTION OF THE DRAWINGS

The invention is described by way of example with reference to the accompanying drawings wherein.

DETAILED DESCRIPTION OF THE PREFERRED EMBODIMENTS

Figure 1:
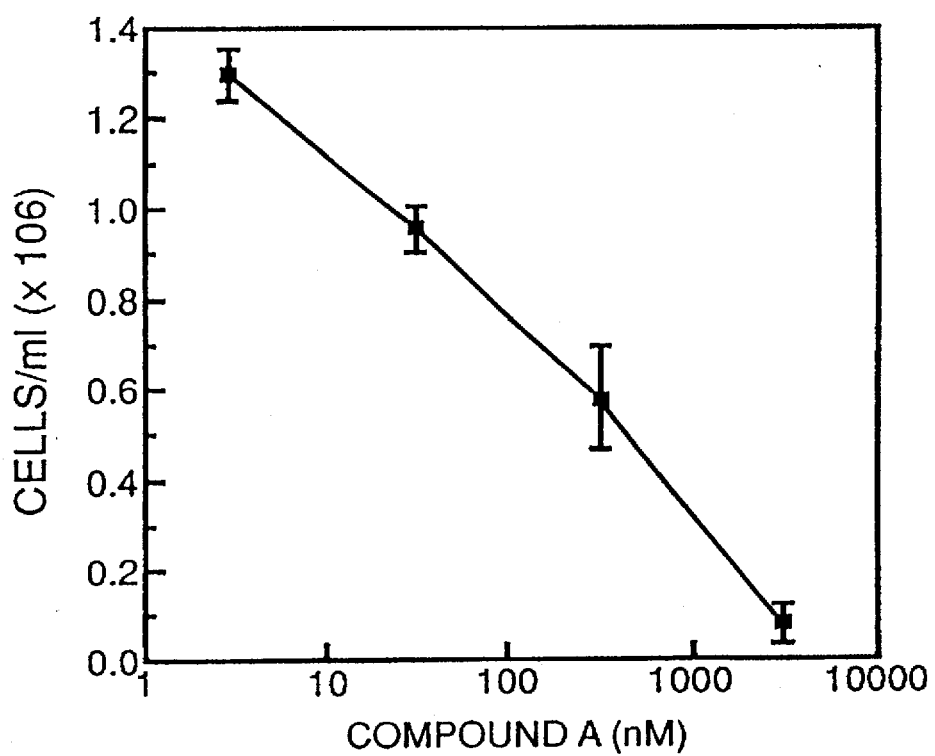
FIG. 1 is a graph representing the viability of the K562 cell line upon exposure to different concentrations of N,N'-decamethylenebis[2-amino-1-(2-imidazolin-2-yl)-2-imidazoline, dihydroiodide (Compound A).

The present invention relates to novel compounds of Formula I

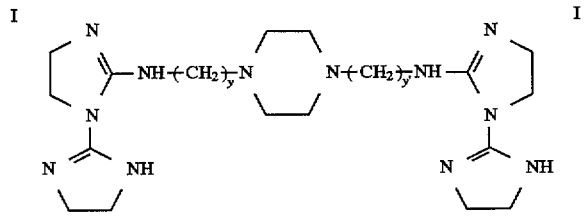

wherein y and y' are each independently an integer from 1 to 8; or a pharmaceutically acceptable salt thereof.

The compounds of Formula I are prepared by treating the compound of Formula IV

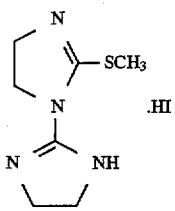

with a compound of Formula V

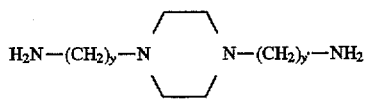

wherein
y and y' are as defined above in a solvent such as, for example, water, acetonitrile, dimethylformamide, dimethylacetamide, and the like optionally in the presence of a base such as an organic base, for example, triethylamine and the like at about room temperature to about the reflux temperature of the solvent to afford a compound of Formula I.

The compound of Formula IV is disclosed in Wittekind R. R., et al., *J. Org. Chem.* 38:1641–1645 (1973).

A compound of Formula V is either known or capable of being prepared by methods known in the art.

A still further embodiment of the present invention relates to novel methods of treating proliferative diseases or viral, inflammatory, allergic and cardiovascular diseases, and restenosis. The treatment comprises administering in unit dosage form to a mammal in need of said treatment a therapeutically effective amount of a compound of Formula I.

The treatment also comprises administering in unit dosage form to a mammal in need of said treatment a therapeutically effective amount of a compound of Formula II

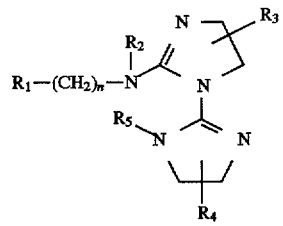

wherein
$R_1$ is hydrogen, lower alkyl, cycloalkyl, aryl, substituted aryl, heterocyclic, substituted heterocyclic, or aryloxy;
$R_2$ is hydrogen, lower alkyl, aryl and substituted aryl; or
$R_1$ and $R_2$ taken together with the nitrogen atom to which they are attached my form a heterocyclic ring;
$R_3$, $R_4$, and $R_5$ are each independently hydrogen, lower alkyl, aryl, or substituted aryl;
n is an integer from 0 to 11.

In the definitions for $R_1$, $R_2$, $R_3$, $R_4$, and $R_5$, the term "lower alkyl" includes lower aliphatic hydrocarbons having 1 to 6 carbon atoms in the carbon chain. It includes straight chain as well as branched chain radicals. The term also includes, for example, methyl, ethyl, n-propyl, isopropyl, n-butyl, isobutyl, n-pentyl, n-hexyl, and the like. The term "cycloalkyl" encompasses saturated monocyclic groups having from 3 to 12 carbon atoms, such as cyclopropyl, cyclobutyl, cyclopentyl, cyclohexyl, cycloheptyl, cyclooctyl, cyclododecyl, and the like. The term "heterocyclic" encompasses monocyclic hetero rings having at least one hetero atoms in the ring which my be either nitrogen, oxygen, or sulfur. Representative heterocyclics falling within this definition are, for example, aziridinyl, azetidinyl, pyrrolyl, pyrrolidinyl, morpholino, thienyl, furyl, pyridyl, piperidyl, indolyl, and the like. Additionally, these heterocyclic rings may have further substituents in their ring portions by groups such as hydrogen, halogen, lower alkyl, and lower alkoxy. The term "aryl" denotes a monocyclic or bicyclic hydrocarbon radical, preferably of 6 to 10 carbon atoms such as, for example, phenyl, naphthyl, and the like. The term "substituted aryl" as used herein includes aryl as defined above in which one or more of the hydrogen atoms of the aryl portion have been substituted by groups such as, halogen, hydroxyl, lower alkyl, trifluoromethyl, amino, substituted amino, or lower alkoxy. The term "aryloxy" means o-aryl as defined above for aryl. The term "lower alkoxy" means o-lower alkyl as defined above for lower alkyl.

The term "mammal" includes humans.

As indicated earlier, the methods for preparing the compounds of Formula II have previously been disclosed in issued U.S. Pat. Nos. 3,666,767, 3,798,232, 3,835,142, 3,840,554, and 3,927,022. These patents are hereby incorporated by reference. The definitions for $R_1$, $R_2$, $R_3$, $R_4$, and $R_5$, and n as used hereinafter have the same meanings as defined above.

The treatment also comprises administering in unit dosage form to a mammal in need of said treatment a therapeutically effective amount of a compound of the following Formula III

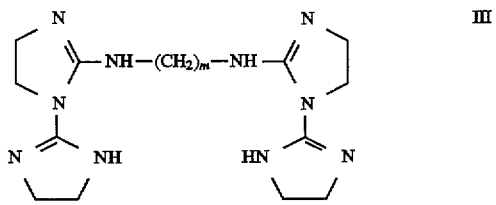

wherein m is an integer from 4 to 12.

As indicated earlier, the methods for preparing the compounds of Formula III have previously been disclosed in issued U.S. Pat. No. 3,905,992. This patent is hereby incorporated by reference.

Structures represented by I and Ia and by II and IIa and by III and IIIa are tautomers; i.e., there is a dynamic equilibrium between each pair of structures shown. When any single member of a tautomeric pair is described, it will be understood that the other tautomer is also described thereby

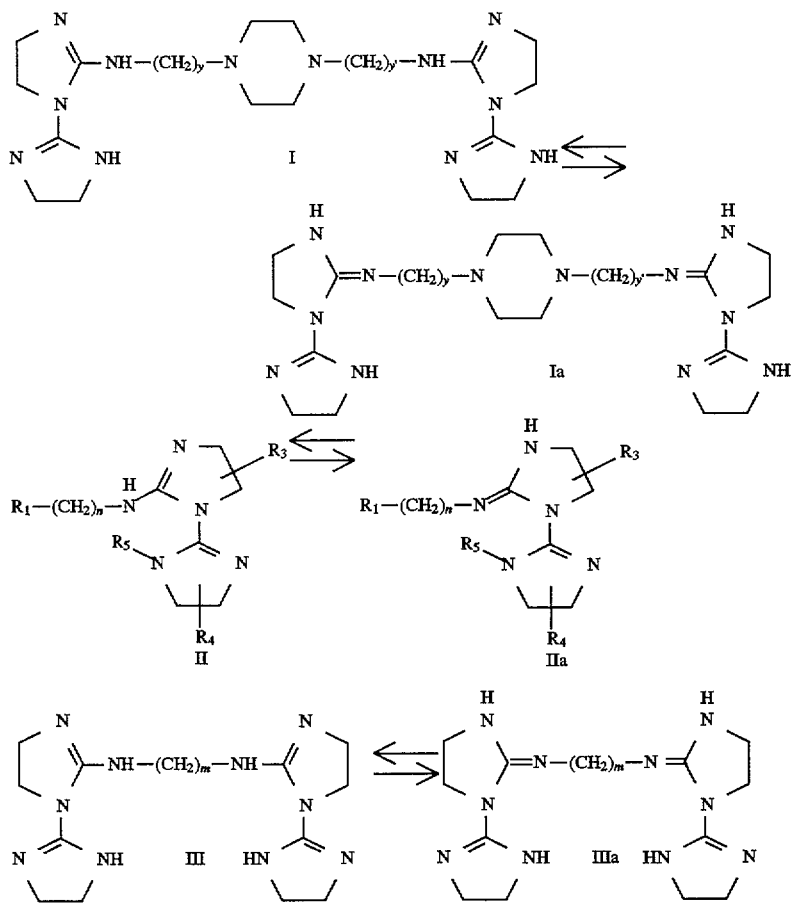

It should be understood that the present invention is not limited to these additional specific compounds disclosed, but also include the different salt and optically active forms as well as solvates and hydrates of these compounds that one skilled in the art would recognize.

The usefulness of the compounds of Formulas I, II, and III above, and the derivatives or salts of each thereof, as agents for treating proliferative diseases or viral, inflammatory, allergic and cardiovascular diseases, and restenosis is demonstrated in standard pharmacologic test procedures.

The compounds of the invention are capable of further forming pharmaceutically acceptable acid addition salts. All of these forms are within the scope of the present invention.

Pharmaceutically acceptable acid addition salts of the compounds of Formulas I, II, and III include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate,. monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge SM, et al, "Pharmaceutical Salts," *J. of Pharma. Sci.* 66:1 (1977)).

The acid addition salts of said basic compounds are prepared by contacting the free-base form with a sufficient amount of the desired acid to produce the salt in the conventional manner. The free-base form may be regenerated by contacting the salt form with a base and isolating the free base in the conventional manner. The free-base forms differ from their respective salt forms somewhat in certain physical properties such as solubility in polar solvents, but otherwise the salts are equivalent to their respective free base for purposes of the present invention.

The compounds of the invention may possess chiral centers and each center may exist in the (R) or (S) configuration. The present invention includes, therefore, all enantiomeric and diastereomeric forms as well as the appropriate mixtures thereof.

The compounds may be administered intravenously, orally or parenterally or by direct injection into the target organ. The usual human dosage ranges for a 80 kg subject are from about 1 mg to about 1 g per day (0.01 mg to 10 mg per kg of weight per day), preferably about 10 mg to about 100 mg per day (0.1 mg to 1.0 mg per kg of weight per day), optionally in divided portions.

The above employed pharmaceutical compositions are produced by formulating a compound of the foregoing formulae (active ingredient) in dosage unit form with a pharmaceutical carrier. Some examples of dosage unit forms are tablets, capsules, lozenges, and pills; as well as powders and aqueous and nonaqueous oral solutions and suspensions, transdermal systems, and parenteral solutions, packaged in containers containing either one or some larger number of dosage units and capable of being subdivided into individual doses by such means as measurement into a teaspoon or other standard container. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc, stearic acid; magnesium stearate; vegetable oils such as peanut oil, cottonseed oil, sesame oil, olive oil, corn oil, and oil of theobroma; propylene glycol; glycol; glycerine, sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primarily liquid composition. The most satisfactory compositions are those in which a much higher proportion of the active ingredient is present. The compositions of the invention preferably contain from 2 mg to 1.0 g of the active ingredient per dosage unit so that the entire amount to be administered during a day can be made up from a reasonable number of dosage units.

Among the preferred compounds in this invention for inhibiting the association of the abl SH-2 domains with the EGFR are as follows:

2-(Heptylamino)-1-(2-imidazolin-2-yl)-2-imidazoline, monohydroiodide;

N,N'-Tetramethylenebis[2-amino-1-(2-imidazolin-2-yl)-2-imidazoline, dihydroiodide;

N,N'-Pentamethylenebis[2-amino-1-(2-imidazolin-2-yl)-2-imidazoline, dihydroiodide;

N,N'-Hexamethylenebis[4,5-dihydro-1-(2-imidazolin-2-yl)-2-imidazoline, dihydroiodide;

2-Cyclododecylamino-1-(2-imidazolin-2-yl)-2-imidazoline, monohydroiodide;

N,N'-Heptamethylenebis[2-amino-1-(2-imidazolin-2-yl)-2-imidazoline, dihydroiodide;

N,N'-Octamethylenebis[2-amino-1-(2-imidazoline-2-yl)-2-imidazoline, dihydroiodide;

N,N'-Decamethylenebis[2-amino-1-(2-imidazolin-2-yl)-2-imidazoline, dihydroiodide;

2-(Heptadecylamino)-1-(2-imidazolin-2-yl)-2-imidazoline, monohydroiodide;

2-[(3,4-Dimethoxyphenethyl)amino]-1-(2-imidazolin-2-yl)-2-imidazoline;

N,N'-Nonamethylenebis[2-amino-1-(2-imidazolin-2-yl)-2-imidazoline, dihydroiodide;

N,N'-Undecamethylenebis[2-amino-1-(2-imidazolin-2-yl)-2-imidazoline, dihydroiodide;

N,N'-Dodecamethylenebis[2-amino-1-(2-imidazolin-2-yl)-2-imidazoline, dihydroiodide;

(4,5,4',5'-Tetrahydro-3H,1'H-[1,2']biimidazolyl-2-ylidene)-tridecyl-amine; and 2-(3-{4-[3-(4,5,4',5'-Tetrahydro-3H,1'H-[1,2'] biimidazolyl-2-ylideneamino)-propyl]-piperazin-1-yl}-propylimino)-2,3,4,5,4',5'-hexahydro-1'H-[1,2'] biimidazolyl.

As will be shown by the data presented herein, the compounds of the present invention are potent inhibitors of [$^{35}$S]abl SH-2 interactions with the activated EGF receptor, and are thus effective in interfering with or modulating the association of the oncogene with its cellular effector(s). The compounds of the present invention are thus useful in pharmaceutical formulations for the treatment of diseases caused by malignant signal transduction pathways dependent upon such interactions.

The following examples illustrate the methods of using N,N'-piperazinylbis[2-amino-1-(2-imidazolin-2-yl)-2-imidazolines], 2-amino-1-(2-imidazolin-2-yl)-2-imidazolines, and N,N'-alkylenebis[2-amino-1-(2-imidazolin-2-yl)-2-imidazolines], as antagonists of SH-2 binding and other therapeutic uses. The examples are given to illustrate particular compositions and methods within the scope of the present invention and are not intended to limit the scope of the present invention.

EXAMPLE 1

The ability of some of the preferred compounds of the present invention to inhibit SH-2 interactions with activated tyrosine kinase receptors was measured using an in vitro biological assay. The test assesses the ability of a test compound to inhibit the interaction of [$^{35}$S]abl SH-2 with activated EGF receptors, or with other receptor tyrosine kinases.

Biological Assay

A bacterial glutathione-S-transferase fusion protein, containing the SH-2 domain of abl, is labelled in vivo with $^{35}$S. Phosphorylated EGFR is purified from EGF-treated 3T3 cells transfected with the human EGFR by precipitation with anti-EGFR antisera. The resulting immune complex is bound to protein A—Sepharose beads. Binding of the $^{35}$S labelled abl fusion protein (77 nM) to the purified EGFR beads complex (approximately 1 μg of receptor/assay) is allowed to proceed to equilibrium (30 minutes) in a total volume of 0.4 mL, in the presence of the test compounds. Bound $^{35}$S fusion protein is separated from free by filtration through 0.65 μ DUPP filters, and radioactivity is determined by scintillation counting.

Results of the binding study are expressed in Table 1 as IC$_{50}$ values, i.e., the concentration of test compound required to inhibit [$^{35}$S]abl SH-2 interactions with the activated EGF receptor. These results show that representative compounds of the invention were effective in inhibiting the binding of the SH-2 domain of abl to EGF receptor in the presence of the indicated concentrations of test compounds.

TABLE 1

| Structure | n | IC$_{50}$ |
|---|---|---|
| H$_3$C—(CH$_2$)$_n$—N=C(imidazoline)-N(tetrahydropyrimidine with NH) | 6 | 10–100 μM |
| bis(tetrahydropyrimidine-guanidine)-N—(CH$_2$)$_n$—N=(imidazoline with tetrahydropyrimidine) | 4 | 27 μM |
| bis(tetrahydropyrimidine-guanidine)-N—(CH$_2$)$_n$—N=(imidazoline with tetrahydropyrimidine) | 5 | 259 μM |
| bis(tetrahydropyrimidine-guanidine)-N—(CH$_2$)$_n$—N=(imidazoline with tetrahydropyrimidine) | 6 | 100 nM |
| (cyclododecyl)-N=(imidazoline)-N(tetrahydropyrimidine with NH) | | >100 μM |
| bis(tetrahydropyrimidine-guanidine)-N—(CH$_2$)$_n$—N=(imidazoline with tetrahydropyrimidine) | 7 | 38 μM |
| bis(tetrahydropyrimidine-guanidine)-N—(CH$_2$)$_n$—N=(imidazoline with tetrahydropyrimidine) | 8 | 33 μM |

TABLE 1-continued

| Structure | n | IC$_{50}$ |
|---|---|---|
| [structure] | 10 | 50 nM |
| [structure] | 12 | 50 μM |
| [structure] | 16 | 1.32 μM |
| [structure] | 9 | 1.3 μM |
| [structure] | 11 | 600 nM |
| [structure] | 12 | 1.2 μM |
| [structure] |  | 10 μM |

EXAMPLE 2

SH-2 tyrosine kinase inhibitors may block the signal transduction pathways for platelet derived growth factor ("PDGF") and fibroblast growth factor ("FGF"), which have been implicated in the control of smooth muscle cell proliferation. The ability of some of the preferred compounds of the present invention to inhibit smooth muscle cell (SMC) proliferation stimulated by PDGF or serum was measured using the biological assay discussed below.

[$^3$H]Thymidine Incorporation Assay

Rat Aortic Smooth Muscle Cells (RASMC) were plated into a 24-well plate (30,000 cells/well) in DMEM with 10% Fetal Bovine Serum (FBS). After 4 days cells reached confluence and were made quiescent by incubation in DMEM/F12 medium (Gibco) containing 0.2% FBS for another 2 days. Incubation with the growth factors, PDGF-BB and bFGF as well as FBS, and test compound was carried out in 0.5 mL/well serum-substituted medium (DMEM/F12+1% CPSR-2 from Sigma) for 22 hours. After 18 hours, 0.25 µCi/well [$^3$H]thymidine was added. Four hours later the incubation was stopped by removing the radioactive media, washing the cells twice with 1 mL cold phosphate-buffered saline, and then washing 2 times with cold 5% trichloroacetic acid. The acid-insoluble fraction was lysed in 0.75 mL 0.25N NaOH and the radioactivity determined by liquid scintillation counting.

Cell Culture

Smooth muscle cells were isolated from the thoracic aorta of rats (RASMC) and explanted according to the method of Ross, et al., *Cell Biology* 50:172–186 (1971). Cells were grown in Dulbecco's modified Eagle's medium (DMEM, Gibco) containing 10% fetal calf serum (FBS, Hyclone, Logan, Utah), 1% glutamine (Gibco), and 1% penicillin/streptomycin (Gibco). Cells were identified as smooth muscle cells by their "hill and valley" growth pattern and by fluorescent staining with a monoclonal antibody specific for SMC α-actin (Sigma). RASMC were used between passages 5 and 20 for all experiments. Test compounds were prepared in dimethylsulfoxide (DMSO) in order to achieve consistency in the vehicle and to ensure compound solubility. Appropriate DMSO controls were simultaneously evaluated with the test compounds.

The results of the cellular proliferation assay are expressed in Table 2 as $IC_{50}$ values, i.e., the concentration of test compound required to inhibit [$^3$H]thymidine incorporation into smooth muscle cells. These results showed that representative compounds of the invention were effective in inhibiting smooth muscle cell proliferation stimulated with PDGF or serum in the presence of the indicated concentration of test compounds.

TABLE 2

| Smooth Muscle Cell Proliferation Assay (Rat Aortic SMC) | | | |
|---|---|---|---|
| Structure | n | $IC_{50}$ (serum) | $IC_{50}$ (PDGF) |
| 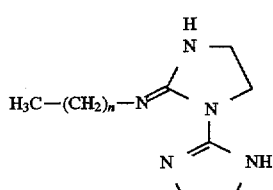 | 6 | 6.4 µM | 3.0 µM |
| 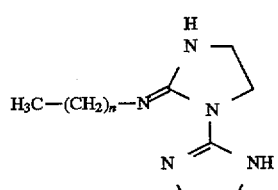 | 16 | <1.0 µM | <1.0 µM |
| 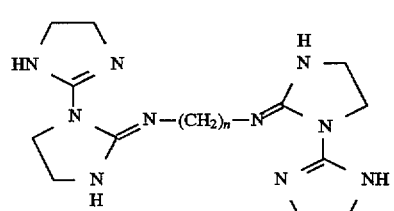 | 5 | >100 µM | 74.0 µM |

TABLE 2-continued

Smooth Muscle Cell Proliferation Assay (Rat Aortic SMC)

| Structure | n | IC$_{50}$ (serum) | IC$_{50}$ (PDGF) |
|---|---|---|---|
| 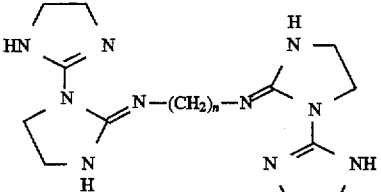 | 8 | 62.0 µM | 40.0 µM |
| 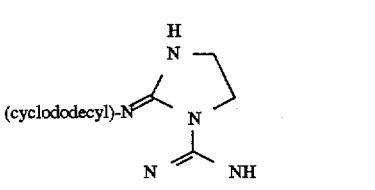 | | 1.1 µM | <1.0 µM |
| 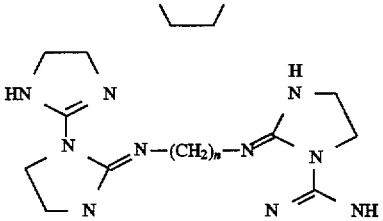 | 10 | 5.0 µM | 2.8 µM |

EXAMPLE 3

Various procedures were utilized to identify the sensitivity of certain cell lines to the compounds of the present invention.

In one screen, K562 human erythroleukemic cells were seeded at 6×10$^4$ cells/mL in RPMI 1640 medium containing 10% fetal bovine serum. These cells score positively for the Philadelphia chromosome, and are known to be transformed by the bcr-abl oncogene. At the time of seeding, test compound, or vehicle (DMSO), were added. Cells were counted 4 days after seeding using a hemocytometer.

The results of this experiment for a representative compound of the present invention appears in Table 3. Test Compound A is N,N'-decamethylenebis[2-amino-1-(2-imidazolin-2-yl)-2-imidazoline, dihydroiodide. The inhibition of growth of tumor cells is expressed as IC$_{50}$ values; i.e., the concentration of test compound required to inhibit growth of the tumor cells by 50%.

TABLE 3

| Cell | IC$_{50}$ (µM) Test Compound A |
|---|---|
| K562 | 0.6 |
| KG-1A | 100 |
| MOLT-4 | 2.1 |
| A431 | 4.4 |
| SWISS 3T3 | >>50 |
| HCT-8 | 6.6 |
| L1210 | 1.0 |
| MCF-7 | 7.8 |

TABLE 3-continued

| Cell | IC$_{50}$ (µM) Test Compound A |
|---|---|
| MDA-231 | 14 |
| MDA-468 | 0.9 |
| NIH 2.2 | >>25 |
| NIH EGF-R | >>25 |

K562 = human chronic myelogenous leukemia; expresses p210$^{bcr-abl}$.
KG-1A = human acute myelogenous leukemia; no bcr-abl.
MOLT-4 = human acute lymphoblastic leukemia; no bcr-abl.
A431 = human epidermoid carcinoma; overexpresses EGF receptor.
SWISS = mouse fibroblast.
HCT-8 = human colon carcinoma; 18,000 EGF receptors/cell.
L1210 = mouse lymphocytic leukemia.
MCF-7 = estrogen-dependent breast adenocarcinoma; 3000 EGF receptors/cell, some erbB-2.
MDA-231 = breast adenocarcinoma; moderate EGFR and erbB-2.
MDA-468 = estrogen independent breast adenocarcinoma; overexpresses EGF receptor.
NIH 2.2 = mouse fibroblast; no EGF receptor.
NIH EGF-R = mouse fibroblast; high expression of EGF receptor.

EXAMPLE 4

In this example, an experiment was conducted to determine the inhibition of the growth of tumor cells from the K562 cell line upon exposure to Test Compound A specified in Example 3. The screen was conducted as described in Example 3.

Figure 2:
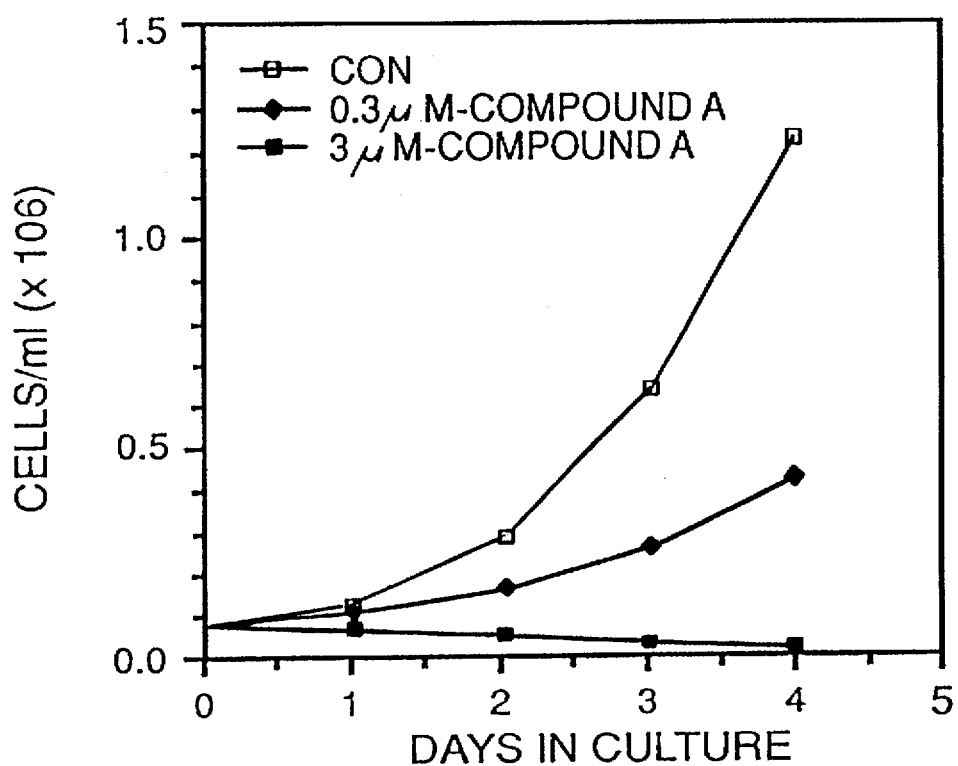
FIG. 2 is a graph representing the viability of the K562 cell line over time after exposure to different concentrations of N,N'-decamethylene-bis[2-amino-1-(2-imidazolin-2-yl)-2-imidazoline, dihydroiodide (Compound A).
Figure 3:
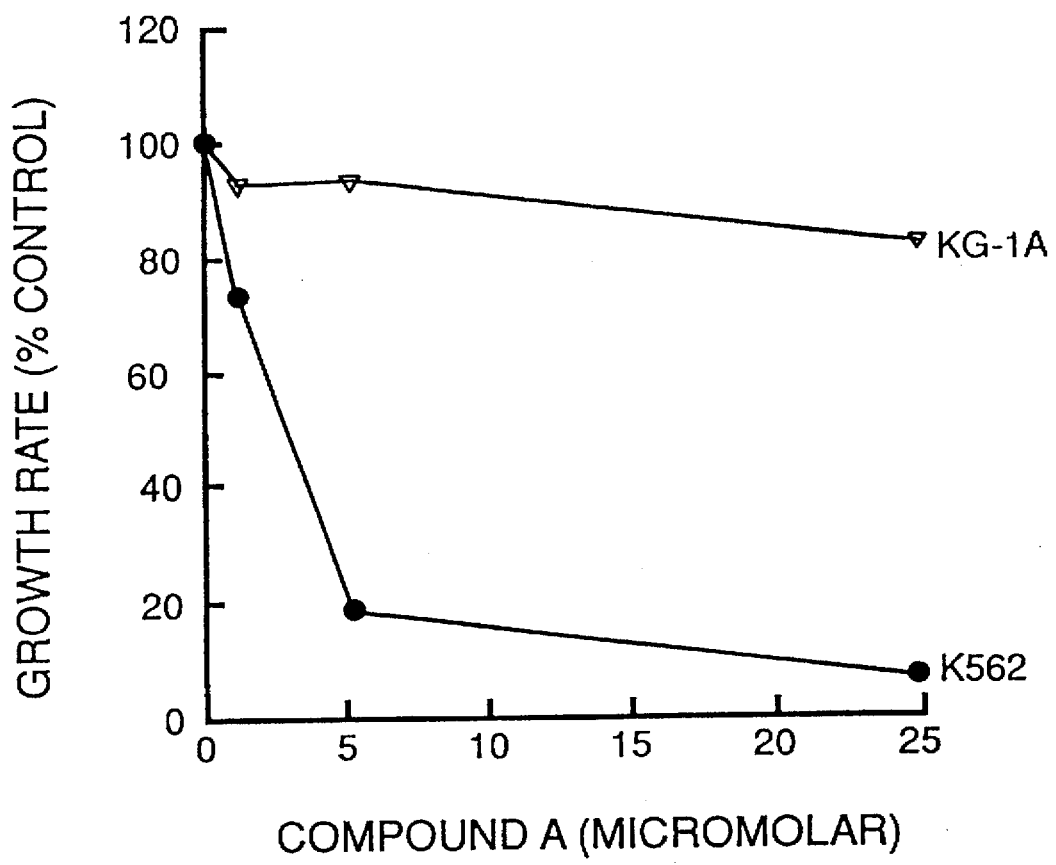
FIG. 3 is a graph representing the effect of N,N'-decamethylenebis[2-amino-1-(2-imidazolin-2-yl)-2-imidazoline, dihydroiodide (Compound A) on the proliferation of the K562 and KG-1A cell lines.

The results of this experiment are illustrated by FIGS. 1 to 3. In FIG. 1, the viability of the K562 cell line was shown to steadily decline upon exposure to increased concentrations of N,N'-decamethylenebis-[2-amino-1-(2-imidazolin-2-yl)-2-imidazoline, dihydroiodide (Compound A).

In FIG. 2, the viability of the K562 cell line over time was shown to have varied upon exposure to different concentrations of the test compound, N,N'-decamethylenebis[2-amino-1-(2-imidazolin-2-yl)-2-imidazoline, dihydroiodide (Compound A). Exposure to 3 µM of the test compound had a substantially greater effect at decreasing the viability of the K562 cell line than did exposure to 0.3 µM of the test compound when compared against a control.

In FIG. 3, the test compound, N,N'-decamethylenebis[2-amino-1-(2-imidazolin-2-yl)-2-imidazoline, dihydroiodide (Compound A), was shown to have differing effects on the Kg-1A and K562 cell lines. At a wide range of concentrations of the test compound, the growth rate of the K562 cell line was substantially decreased, whereas at even a wide range of concentrations of the test compound, the growth rate of the KG-1A cell line was only slightly decreased.

EXAMPLE 5

2-(3-{4-[3-(4,5,4',5'-Tetrahydro-3H,1'H-[1,2']biimidazolyl-2-ylideneamino)-propyl]-piperazin-1-yl}-propylimino)-2,3,4,5,4',5'-hexahydro-1'H-[1,2']biimidazolyl A solution of 1-(2-imidazolin-2-yl)-2-(methylthio)-2-imidazoline hydroiodide (Wittekind, R. R., et al., *J. Org. Chem.* 38:1641–1645 (1973)), (1 g, 3.3 mmol) and (bis-3-amino propyl)piperazine (0.33 g, 1.7 mmol) in acetonitrile (35 mL) was heated at reflux for 6 hours, while a stream of nitrogen gas was bubbled through the reaction vessel. The reaction mixture was allowed to cool to room temperature, the insoluble product collected by filtration, and dried in vacuo to afford 0.12 g of the title compound; mp turned brown at 160° C. Melted >250° C.

C,H,N: calc for $C_{22}H_{40}N_{12}$: 1.31 mol $H_2O$: 1.97 mol HI:
Calcd: C, 35.32; H, 6.01; N, 2.46.
Found: C, 35.30; H, 6.01; N, 22.60.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of treating proliferative disease caused by malignant signal transduction pathways in mammals which comprises administering in unit dosage form to a mammal in need of said treatment a therapeutically effective amount of a compound of Formula III

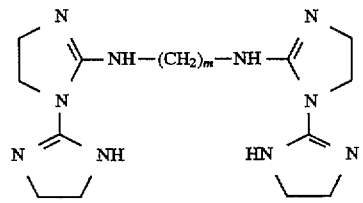

wherein
m is an integer from 4 to 12;
or a pharmaceutically acceptable salt thereof.

2. A method according to claim 1 wherein the method treats tumors.

3. A method according to claim 1 wherein the method treats tumors resulting from the association of abl SH2 domain signaling proteins with tyrosine kinase or oncogenic receptors.

4. A method according to claim 3 wherein the method treats tumors selected from the group consisting of: human chronic myelogenous leukemia; human acute myelogenous leukemia; human acute lymphoblastic leukemia; human epidermoid carcinoma; human colon carcinoma; and breast adenocarcinoma.

5. A method according to claim 1 wherein an individual dose is administered in the range from about 1 mg to about 1 g per day intravenously of a compound of Formula III or a pharmaceutically acceptable salt thereof.

6. A method according to claim 1 wherein an individual dose is in the range from about 1 mg to about 1 g per day parenterally or about 1 mg to about 1 g per day enterally of a compound of Formula III or a pharmaceutically acceptable salt thereof.

7. A method according to claim 1 wherein the compound is selected from the group consisting of:

N,N'-Tetramethylenebis[2-amino-1-(2-imidazolin-2-yl)-2-imidazoline;

N,N'-Pentamethylenebis[2-amino-1-(2-imidazolin-2-yl)-2-imidazoline;

N,N'-Hexamethylenebis[4,5-dihydro-1-(2-imidazolin-2-yl)-2-imidazoline;

N,N'-Heptamethylenebis[2-amino-1-(2-imidazolin-2-yl)-2-imidazoline;

N,N'-Octamethylenebis[2-amino-1-(2-imidazolin-2-yl)-2-imidazoline:

N,N'-Decamethylenebis[2-amino-1-(2-imidazolin-2-yl)-2-imidazoline;

N,N'-Nonamethylenebis[2-amino-1-(2-imidazolin-2-yl)-2-imidazoline;

N,N'-Undecamethylenebis[2-amino-1-(2-imidazolin-2-yl)-2-imidazoline; and

N,N'-Dodecamethylenebis[2-amino-1-(2-imidazolin-2-yl)-2-imidazoline;

or a pharmaceutically acceptable salt thereof.

8. A method according to claim 1 wherein an individual dose is administered in the range from about 10 mg to about 100 mg per day intravenously of a compound of Formula III or a pharmaceutically acceptable salt thereof.

9. A method according to claim 1 wherein an individual dose is in the range from about 10 mg to about 100 mg per day parenterally or about 10 mg to about 100 mg per day enterally of a compound of Formula III or a pharmaceutically acceptable salt thereof.

10. A method of treating diseases by inhibiting the association of a tyrosine phosphorylated protein with SH-2 containing proteins comprising administering to a mammal suffering therefrom a therapeutically effective amount of a compound of Formula III

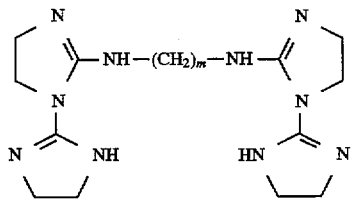

wherein
m is an integer from 4 to 12;
or a pharmaceutically acceptable salt thereof.

11. The method of claim 10 which diseases comprise proliferative diseases.

* * * * *